United States Patent [19]
James et al.

[11] 4,141,351
[45] Feb. 27, 1979

[54] ECG ELECTRODE IMPEDANCE CHECKING SYSTEM AS FOR EMERGENCY MEDICAL SERVICE

[75] Inventors: Gordon W. James, Plantation; David G. Storm, Fort Lauderdale, both of Fla.

[73] Assignee: Motorola, Inc., Schaumburg, Ill.

[21] Appl. No.: 832,320

[22] Filed: Sep. 12, 1977

[51] Int. Cl.² ............................................. A61B 5/04
[52] U.S. Cl. .............................. 128/2.06 R; 324/57 R
[58] Field of Search .................... 128/2.06 E, 2.06 R, 128/2.06 B, 2.06 RB, 2.1 Z; 324/57 R

[56] References Cited
U.S. PATENT DOCUMENTS

| | | | |
|---|---|---|---|
| 3,426,150 | 2/1969 | Tygart | 128/2.1 A |
| 3,495,584 | 2/1970 | Schwalm | 128/2.06 B |
| 3,559,193 | 1/1971 | Savaglio et al. | 128/2.06 B |
| 3,757,778 | 9/1973 | Graham | 128/2.06 B |
| 3,859,988 | 1/1975 | Lencioni, Jr. | 128/2.1 B |
| 3,882,277 | 5/1975 | De Pedro et al. | 128/2.1 X |
| 3,971,366 | 7/1976 | Motoyama | 128/2.1 Z |
| 4,027,663 | 6/1977 | Fischler et al. | 128/2.06 R |

*Primary Examiner*—William E. Kamm
*Attorney, Agent, or Firm*—Margaret Marsh Parker; James W. Gillman

[57] ABSTRACT

A circuit for checking a plurality of impedances having a common connection point as for use in an emergency medical ratio, where the impedance of each ECG electrode contact is automatically and sequentially checked during the initial calibration transmission, using the AC non-polarizing signal which is also used as the ECG subcarrier for the medical data telemetry. The ECG telemetry calibration signal is also processed to provide a sequential switching control. Poor electrode contacts are indicated visually to the paramedic in charge and thus can be corrected before ECG telemetry begins.

12 Claims, 4 Drawing Figures

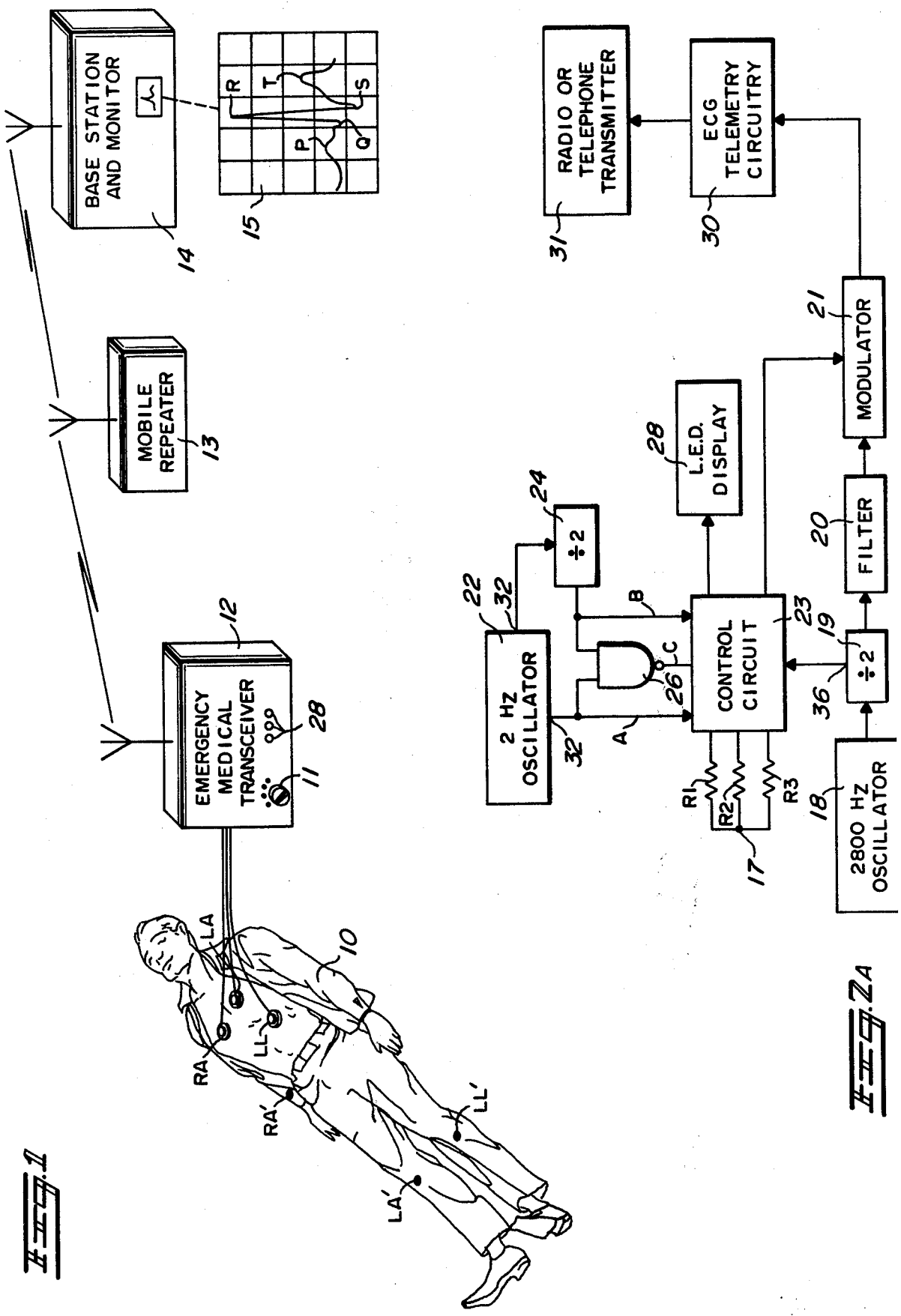

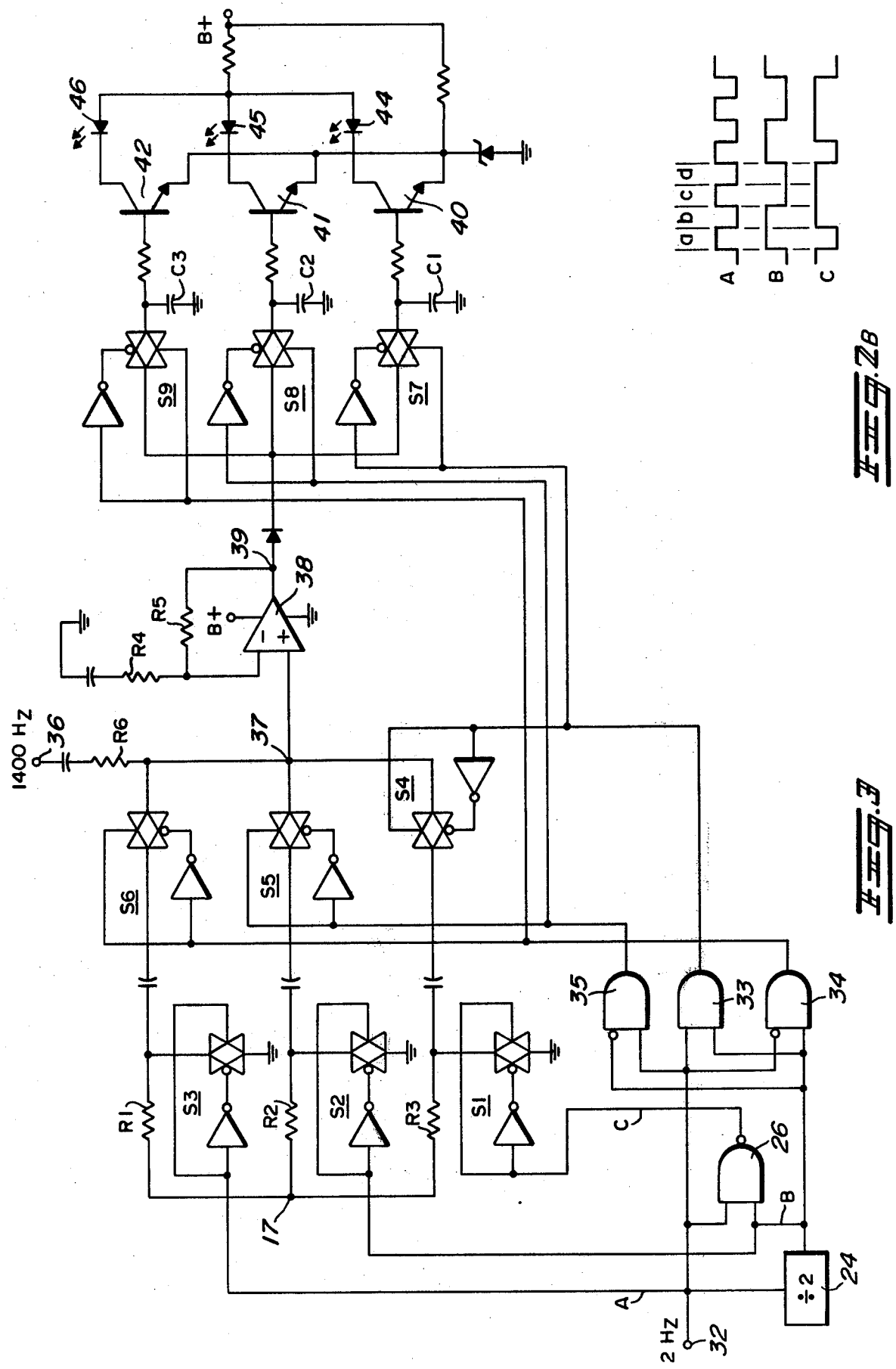

1

ECG ELECTRODE IMPEDANCE CHECKING SYSTEM AS FOR EMERGENCY MEDICAL SERVICE

BACKGROUND OF THE INVENTION

This invention relates to the field of emergency medical radios, and more particularly, to an improved and faster means of checking the ECG electrode impedances before ECG telemetry begins.

Emergency medical radios are known in the art to provide two-way communication between a paramedic team on the scene of an emergency and a hospital, plus the capability of relaying to the hospital vital signs such as electrocardiogram signals (ECG) for expert analysis. After analysis, advice will be transmitted back as to the proper treatment to be administered. Such systems may utilize direct broadcast, relayed broadcast or telephone line transmissions, depending on the circumstances. In the typical operation, a paramedic will make contact with the hospital by voice, send a calibrating signal, test the electrode resistances, then begin the actual telemetry. It is important to test the electrode resistance at the scene, since the paramedic does not see a print out of the ECG signal and would have to be alerted by the hospital if a bad connection or open line existed. Since time, even a few seconds, may be a matter of life or death for an accident or heart attack victim, any time wasted or a faulty transmission could have tragic consequences.

Also in the prior art, electrodes have been checked with direct current, and because of the chemistry involved, a coating which was a semiconductor, could be produced on the electrodes. Thus the level of contact resistance could become higher and higher, with resulting loss of accurate signals.

SUMMARY OF THE INVENTION

It is therefore an object of this invention to provide a faster way of checking electrode resistance as for use in an emergency medical radio system.

It is another object to provide electrode checking without chemical affect on the electrode resistance.

It is a particular object to allow electrode checking during the calibration period of the system.

The above objects and others are provided in a circuit according to the invention by the use of two AC signals already present in the radio. One signal is the audio frequency signal upon which the ECG signals are modulated for telemetry; the other is the calibration signal which is transmitted to the hospital before the ECG signals for the purpose of providing for a reference level substantially equal to a normal ECG level. The latter signal is an extremely low frequency signal and is used in conjunction with control circuitry to provide switching for the electrode checking sequence.

BRIEF DESCRIPTION OF THE DRAWING

FIG. 1 is a general view of the system in operation.
FIG. 2A is a block diagram of the system.
FIG. 2B is a timing diagram of the switching wave forms for FIG. 2A.
FIG. 3 is a logic diagram of the control circuitry with some of the interconnecting elements.

DETAILED DESCRIPTION OF A PREFERRED EMBODIMENT

In FIG. 1 is shown a general system which could utilize the invention, although it is not intended to so limit it. A patient 10 has been coupled to three electrodes, RA, LA, and LL. These symbols are used to designate the three locations shown. Three alternate locations are designated RA', LA' and LL' and may be used if the circumstances warrant. It may be well at this point to explain the use of the term "lead" in electrocardiology. A "lead" signal is that signal developed between two given connections to the patient's body. Thus, with two connections, only one "lead" exists. With three connections or electrodes, three "leads" are available. Four electrodes could provide six "leads".

The use of three electrodes as shown is typical with emergency medical radio equipment, and the circuit of the invention will be described in terms of three electrodes although it not so limited. For each of the three "leads", two of the electrodes are connected to the amplifier inputs and the third electrode acts as a reference ground for the amplifier. The switch 11 has four positions, one for each "lead" and a calibration/electrode checking (CAL/CK) position. For telemetry of the ECG signals, the operator or paramedic will switch to the lead positions as necessary. The CAL/CK position is for the mode in which the circuitry of the invention is operative. The electrodes may be of any suitable type such as silver/silver-chloride, used with a conductive paste. The appropriate areas of the skin of the patient 10 are first cleaned with alcohol. The electrodes marked RA, LA and LL are attached to the skin and connections are made from the electrodes through a switch 11 on a low power emergency medical transceiver 12. The transceiver 12 could communicate by direct transmission to the hospital but more commonly will transmit to a higher powered repeater unit 13 in an emergency vehicle. The repeater 13 will then transmit to and receive from a base station unit 14 as in a hospital. The base unit 14 will be coupled to monitoring equipment including a recording device for the transmitted ECG signal. Two-way voice communication may be provided simultaneously with the ECG transmission. Also included is an enlarged view 15 of a portion of a recorded signal with the sections of one ECG pulse designated by the letters P-T as normally used in cardiology.

FIG. 2A is a block diagram of the circuitry and FIG. 2B is a timing diagram of the switching wave forms used therein. The impedances of the three electrode-to-skin connections are represented by resistors R1, R2 and R3 and the interior of the patient's body is represented in the circuit as the common tie point 17.

Two oscillators are normally used in the unit and their outputs are also utilized in the circuit of the invention. A first oscillator 18, running at approximately 2800 Hz, is divided down to 1400 Hz in a divider ($\div$ 2) 19. A filter 20 removes any residual harmonics from the divider output and the output is coupled to modulator 21. During telemetry, the low frequency ECG signals from the electrodes RA, LA and LL are modulated on the 1400 Hz signal which in turn modulates the RF carrier frequency. Since duplex voice communication is also modulated on the RF carrier, both the transceiver 12 and the receiver at the base station 14 will include filters (not shown) for separating the 1400 Hz carrier signal from the audio channels. A second oscillator 22 provides a 2 Hz signal which is clipped to provide a 1 mv. square wave calibration signal A (see FIG. 2B). As soon as a paramedic has made voice contact with the base station at the hospital, the unit is switched to a calibrate/electrode-check mode. In this mode, the 1 mv. 2

Hz calibration signal is transmitted to the hospital, 1 mv. being the strength of an average ECG signal. During this calibration period the paramedic can be attaching the electrodes to the patient, then checking to see that good contacts have been made. While electrode resistances of as high as 100 K could be used, much lower resistances are necessary for good signal transmission. Obviously an open or intermittent connection cannot be tolerated and must be replaced immediately.

The 2 Hz signal A from the oscillator 22 is utilized for switching control. The signal is coupled directly to a control circuit 23 which also couples it to the modulator 21. The signal A also passes through a second divider ($\div 0\ 2$) 24 and the 1 Hz output B (see FIG. 2B) of the divider 24 is coupled to the control circuit 23. Both signals A and B are coupled to a NAND gate 26. The output C (see FIG. 2B) of NAND gate 26 is thus low only when both signals A and B are high. The use of the signals A, B and C will be explained with respect to FIG. 3. It is to be noted that the values of 2 Hz and 1400 Hz signals are exemplary only, and were chosen because signals at these frequencies were present in the emergency radio apparatus with which the invention is being commercially utilized. The desirable range of values for the switching signal is from 0.25 Hz to 10 Hz, and for the audio frequency carrier, 500 Hz to 10 KHz.

The control circuit 23 is coupled to a visual indicator 28 such as a LED display. During the electrode checking period, the electrode impedances R1-R3 are checked sequentially and any high resistance or open circuit will be indicated by the illumination of the corresponding LED. Thus the paramedic can be certain of having all low resistance electrode contacts before the ECG telemetry proper begins. When the hospital confirms that its equipment is calibrated, the paramedic will switch the unit out of the calibration/electrode-checking mode and switch the various "lead" outputs to the modulator 21. The modulated signal is coupled to ECG telemetry circuitry 30 and to a transmitter 31 which may be radio or telephone as explained hereinabove.

FIG. 3 shows a portion of the control circuitry 23 with an input terminal 32 bringing the signal A from the 2 Hz oscillator 22. Signal A is coupled to the divider 24 and the NAND gate 26 as described hereinabove and is also coupled to control an analog switch S3. The output B of the divider 24 is coupled to control a switch S2 and the output C of the NAND gate 26 controls a switch S1,; i.e., switch S1 will be closed when either A or B is low. Signals A and B are coupled to an AND gate 33 which controls switches S4 and S7. Signals A and B are coupled to an AND gate 34 which controls switches S6 and S9. Signals A and B are coupled to an AND gate 35 which controls switches S5 and S8. A preferred embodiment of the voltage controlled switches S1-S9 would be Motorola integrated circuits MC 14016, each of which contains four such switching circuits.

The switches S1-S6 serve to connect the resistances R1-R3 in various configurations and to couple them to the 1400 Hz reference voltage source 36 in the proper sequence. The voltage at the input 37 of an amplifier 38 then depends on the resistances R1-R3 and their interconnection. The output 39 of the amplifier 38 is coupled to the switches S7-S9 and, through any closed switch S7, S8 or S9, to a corresponding LED driver stage 40, 41 or 42 for driving an LED 44, 45 or 46. The emitters of the driver stages 40, 41 and 42 are coupled to ground through a Zener diode 47.

Operationally, the circuit is perhaps best explained in terms of one set of electrode-to-skin impedances. Referring back to FIG. 2B, R3 will be examined during time period (a), R1 during period (b), R2 during period (c) and no impedances are checked during period (d). Each of the periods a-d is approximately one-half second in duration. Let us assume that R3 is too high, meaning that the electrode RA is making a poor connection to the patient's skin (or that the connecting wire is broken), and that R2 and R1 are within the acceptable range. During time period (a) both signals A and B are high and C is low. Switches S3, S2, S4 and S7 are therefore closed, all other switches being opened. The path from amplifier input 37 through the electrodes to ground will be R3 plus R2 and R1 in parallel and the voltage V37 at input 37 would be $[V36 \times (R1 + 0.5R2)]/[R6 + (R1 + 0.5R2)]$, where $R2 \simeq R3$. If the resistors R1-R3 are essentially equal, the voltage V37 at input 37 would be $[V_{ref} \times (3R/2)]/[R6 + (3R/2)]$. The voltage V39 at the output 39 would be V37 (R5 + R4)/R4. Three capacitors C1-C3 are coupled to ground from the output sides of switches S7-S9 respectively, and when one of the capacitors c1-C3 charges to a potential higher than the sum of the emitter-base drop of the corresponding driver 40, 41 or 42 and the potential drop across the Zener diode 47, the corresponding LED 44, 45, or 46 will glow. Since we have assumed that R1 was either open or too high for satisfactory use, the voltage 37, and thus voltage 38, will be high enough to charge C1 to a voltage sufficient to cause driver stage 40 to conduct and the LED 44 to glow. The value of resistance in R1-R3 which is taken to be acceptable can be determined by the resistors R4, R5 and R6, and by the reference voltage 36.

Since the 1400 Hz voltage is applied to resistors R1-R3 for checking impedance, no "plating" effect can cause the electrode-to-skin resistance to rise during use. Since the two signals necessary for electrode checking are already present in the system, few extra components are required for the circuit of the invention. Most important of all to the patient, the electrode checking is done while the calibration signal is being transmitted, thus no time is lost by a poor or broken connection, when lost time can be a matter of life or death.

Although the circuit of the invention has been shown in the environment of an emergency medical radio, and is highly desirable therein, no limitation thereto is implied, the only limitations being those of the appended claims.

What is claimed is:

1. A circuit for checking a plurality of impedances, the impedances having a common connection point, the circuit comprising in combination:
   a first frequency source;
   first circuit means coupled to the first frequency source for providing a plurality of switching control signals;
   a second frequency source, said second frequency being at least fifty times said first frequency;
   first switching means coupled to the first circuit means and the second frequency source and controlled by the first circuit means for switching the impedances into ones of a plurality of configurations and coupling the second frequency thereto;
   second switching means coupled to and controlled by the first circuit means;
   indicator means including one indicator for each impedance;

enabling means coupled to the outputs of the second switching means and to the indicator means and reference means for enabling one of the indicators when the respective impedance is greater than the predetermined value of impedance.

2. A circuit for checking impedances according to claim 1 and wherein the first circuit means includes divider means for dividing the first frequency by two and a logic gate for providing a signal in response to predetermined logic levels of the first frequency signal and the output signal of the divider means.

3. A circuit for checking impedances according to claim 1 and wherein the configurations of impedances provided by the first switching means are such that if the impedance desired to be checked is greater than the predetermined value, the impedance of the configuration will be increased by the same amount.

4. A circuit for checking impedances according to claim 3 and wherein each configuration comprises the impedance to be checked in series with a parallel combination of at least two of the remaining impedances.

5. A circuit for checking impedances according to claim 1 and wherein the first switching means includes two switches for each impedance to be checked, one of said switches coupled between said second frequency source and a first end of said impedance, and one of said switches coupled between ground and said first end of said impedance, said two switches being closed alternately.

6. A circuit for checking impedances according to claim 5 and wherein the second switching means includes one switch for each impedance, each of said switches being closed when the first said switch for the same impedance in said first switching means is closed.

7. A circuit for checking impedances according to claim 1 and wherein the enabling means includes a DC power source, driver means for each indicator means, and capacitor means coupled to each switch output of the second switching means for receiving and storing sufficient charge for activating said driver means.

8. A circuit for checking impedances according to claim 7 wherein the enabling means further includes a Zener diode, and the driver means are transistors, each transistor base being coupled to the respective switch output of the second switching means, one element of each transistor being coupled to said power supply through the respective indicator and one element of each transistor being coupled to the Zener diode, whereby a transistor will conduct and the associated indicator will indicate when the voltage on the associated capacitor means exceeds the sum of the breakdown voltage of the Zener diode and the diode drop within the transistor.

9. A circuit for checking impedances according to claim 1 and wherein the indicators are light emitting diodes.

10. An electrode impedance checking circuit in an emergency medical radio apparatus, the circuit including in combination:
   a first frequency source;
   first circuit means coupled to the first frequency source for providing a plurality of switching control signals;
   a second frequency source, said second frequency being substantially higher than said first frequency;
   first switching means coupled to the first circuit means and the second frequency source, and controlled by the first circuit means for switching the impedances into ones of a plurality of configurations and coupling the second frequency thereto;
   second switching means controlled by the first circuit means;
   indicator means including one indicator for each impedance;
   reference means for establishing a predetermined value of impedance; and
   enabling means coupled to the outputs of the second switching means and to the indicator means for enabling one of the indicators when the respective impedance is greater than the predetermined value of impedance.

11. An electrode impedance checking circuit according to claim 10 wherein the first frequency source is an oscillator in the radio apparatus for supplying low frequency calibration signals.

12. An electrode impedance checking circuit according to claim 10 wherein the second frequency source is an oscillator in the radio apparatus for supplying a subcarrier signal.

* * * * *